June 16, 1953 W. KORDES Plant Pat. 1,197
ROSE PLANT
Filed June 24, 1952
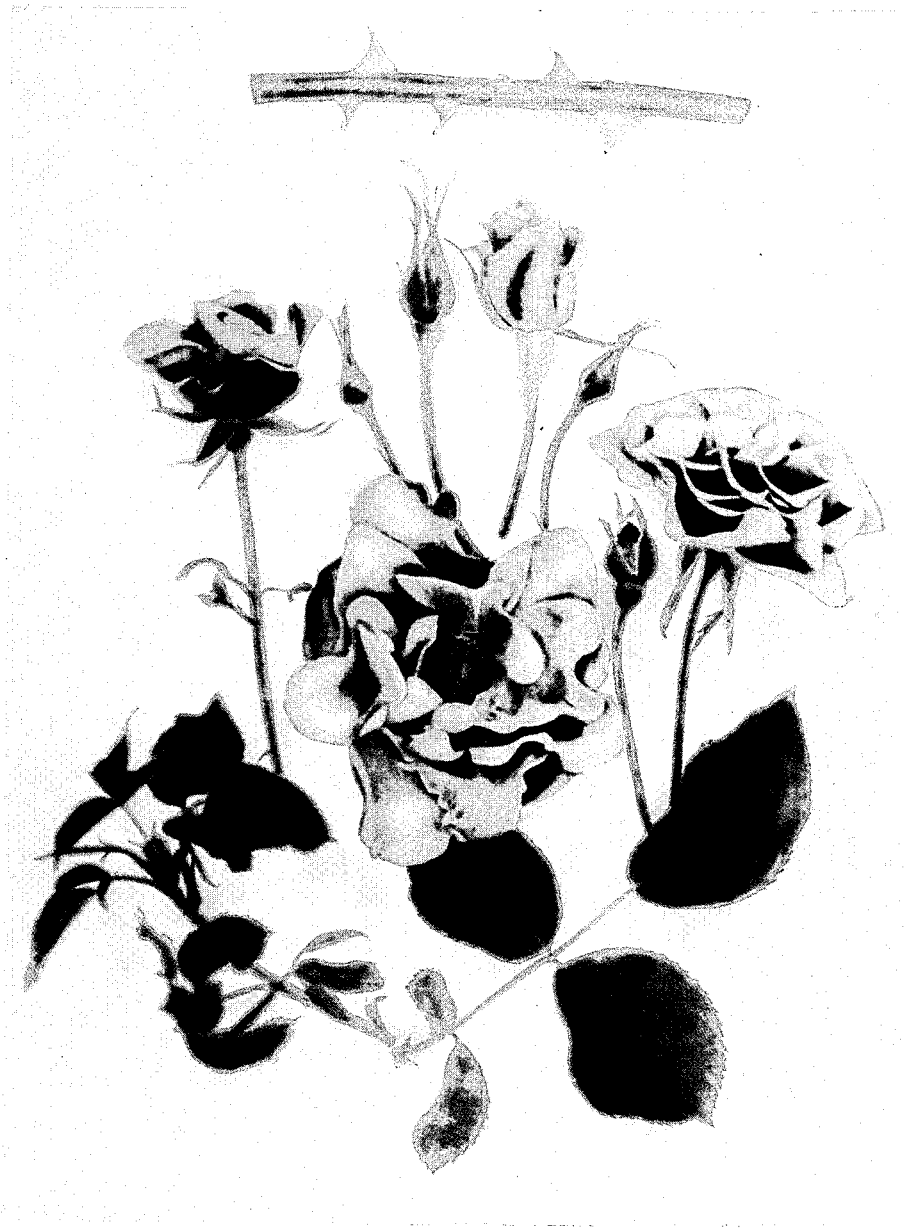
Inventor
Wilhelm Kordes
By Robert Cobb
Attorneys.

Patented June 16, 1953

Plant Pat. 1,197

UNITED STATES PATENT OFFICE 1,197

ROSE PLANT

Wilhelm Kordes, Holstein, Germany, assignor to Jackson & Perkins Company, Newark, N. Y., a corporation of New York Application June 24, 1952, Serial No. 295,376

1 Claim. (Cl. 47—61)

The present invention relates to a new and distinct variety of rose plant of the large-flowered polyantha class, originated by me by crossing an unnamed and unpatented seedling of "Baby Chateau" (unpatented) × "Else Poulsen" (unpatented) with the variety "Sondermeldung" (unpatented).

The primary objective of this breeding was to produce in the seedling of "Baby Chateau" × "Else Poulsen" a sharper color in the flowers. This objective was fully achieved by the use of the variety "Sondermeldung" as the pollen parent in breeding the new variety herein.

My new variety is primarily characterized by the sharp coloring and non-fading habit of its flowers which may be said to be generally of the "Else Poulsen" type, the coloring of the flowers being Spectrum Red in general tonality and substantially non-fading even in the hottest sun. My new variety is also relatively long-lasting for a rose of this type and form, and the petals of its flowers are characterized by a unique waving which seems to accentuate the coloring thereof. These characteristics are combined with a bushy and upright habit of growth, and altogether, the characteristics clearly distinguish my new variety from its parents, as well as from all other varieties of its class.

Asexual reproduction of the new variety by buddings at both Newark, New York, and Pleasanton, California, U. S. A., shows that the foregoing characteristics and distinctions come true to form and are established and transmitted through succeeding propagations.

The accompanying drawing shows typical specimens of my new variety, with the flowers and foliage in different stages of development.

The following is a detailed description of my new variety, with color terminology in accordance with Ridgway's Color Standards and Nomenclature:

Parentage: Seedling.

*Seed parent.*—A seedling of "Baby Chateau" × "Else Poulsen."

*Pollen parent.*—"Sondermeldung."

Classification:

*Botanic.*—Large-flowered polyantha.

*Commercial.*—Floribunda.

*Flower*

(Observations made in a greenhouse at Newark, New York, in the early morning, near the middle of the month of May).

Blooming habit: Recurrent—continuous.

Bud:

*Size.*—Medium.

*Form.*—Ovoid; is not affected by wet or hot weather.

*Color.*—When sepals first divide—Victoria Lake, Plate 1. When petals begin to unfurl—Carmine, Plate 1. When half blown: inside of petals—Carmine, Plate 1; reverse of petals—Spectrum Red, Plate 1.

*Sepals.*—Slightly branched; "hood" above bud; curl back when petals begin to unfurl. Color: inside—Kildare Green, Plate 31; outside—Absinthe Green, Plate 31.

*Calyx.*—Shape—pear. Size — small. Aspect—smooth. Odor when rubbed—none. Color—Absinthe Green, Plate 31.

*Peduncle.* — Length — medium. Aspect — prickly. Strength—stiff; slender. Color—Biscay Green, Plate 17.

*Opening.*—Opens up well; is not affected by adverse weather conditions.

Bloom:

*Size.*—Medium. Average size when fully expanded—3 inches to 3½ inches.

*Borne.*—Singly and sometimes several together; in irregular clusters.

*Stems.*—Long; strong.

*Form.*—When first open—cupped. Permanence—flattens.

*Petalage.*—Semi-double (full but open center); 3 rows of wavy petals with open center. Number of petals under normal conditions—15 to 20.

*Color.*—Center of flower—Spectrum Red, Plate 1. Outer petals—Spectrum Red, Plate 1, lightly overcast with Scarlet Red, Plate 1. Base of petals (aiglet)—Napthalene Yellow, Plate 16. Inside of petals—Spectrum Red, Plate 1, with a slight cast of Tyrian Rose, Plate 12, extending from the base over the lower third of the petal. Reverse of petals—Pomegranate Purple, Plate 12, slightly overcast with Rose Red, Plate 12. General tonality from a distance—Spectrum Red, Plate 1.

*Discoloration.*—Holds its color very well; does not fade in sun. General tonality at end of first day—Spectrum Red, Plate 1. Second day—Spectrum Red, Plate 1, lightly overcast with Scarlet Red, Plate 1. Third day—Spectrum Red, Plate 1, lightly overcast with Scarlet Red, Plate 1.

Petals:

*Texture.*—Leathery; is not affected by wet or hot weather.

*Appearance.* — Inside—shiny; outside—velvety.

*Form.*—Oval; slightly notched; with wavy-like petals, like the petals of rose variety "Permanent Wave" (Plant Patent No. 107).

*Arrangement.*—Imbricated (regularly arranged shingle-like). Petaloids in center—few; small.

*Persistence.*—Drop off cleanly.

*Fragrance.*—Slight. Nature—fruity (Russet apple).

*Lasting quality.*—On the plant and as cut flower—long.

*Genital organs*

Stamens, anthers: Large; many.

*Arrangement.*—Regular around styles.

*Color.*—Apricot Buff, Plate 14.

Stamens, filaments (threads):

*Length.*—Medium.

*Color.*—Carmine, Plate 1.

Pollen: Color—Maize Yellow, Plate 4.

Styles: Bunched; uneven length; short; thin.

Stigmas: Color—Primrose Yellow, Plate 30.

Ovaries: All enclosed in calyx.

*Plant*

Form: Bush.

Growth: Vigorous; upright; bushy.

Foliage: 5 to 7 leaflets.

*Size.*—Medium.

*Quantity.*—Normal abundance.

*Color.*—New foliage: upper side—Yellowish Oil Green, Plate 5, lightly overcast with Brazil Red, Plate 1; under side—Oxblood Red, Plate 1. Old foliage: upper side—Cress Green, Plate 31; under side—Light Cress Green, Plate 31.

*Shape.*—Oval pointed.

*Texture.* — Upper side — leathery. Under side—smooth. Ribs and veins—ordinary.

*Edge.*—Serrated (saw toothed).

*Serration.*—Double; small.

*Leaf stem.*—Color—Deep Chrysolite Green, Plate 31. Under side—smooth.

*Stipules.*—Medium length; slightly bearded.

Wood:

*New wood.*—Color—Hay's Russet, Plate 14. Bark—smooth.

*Old wood.*—Color—Biscay Green, Plate 17. Bark—smooth.

Thorns:

*Thorns.*—Quantity—on main stalks from base and on laterals from stalk—ordinary. Form — broad base; medium length; hooked downward. Color when young—Carmine, Plate 1. Position—irregular.

*Prickles and short needles.*—On main stalks and on laterals. None.

I claim:

A new and distinct variety of rose plant of the large-flowered polyantha class, substantially as herein shown and described, characterized as to novelty particularly by the relatively sharp and non-fading Spectrum Red general color tonality of its blooms, by the waved form of the petals of its bloom which tends to accentuate the color, by the long-lasting quality of its blooms, and by the bushy and upright habits of growth of the plant.

WILHELM KORDES.

No references cited.